(12) United States Patent
Devito

(10) Patent No.: US 9,510,864 B2
(45) Date of Patent: Dec. 6, 2016

(54) ASSEMBLY FOR TREATING AN ISTHMIC FRACTURE

(71) Applicant: Dennis P. Devito, Atlanta, GA (US)

(72) Inventor: Dennis P. Devito, Atlanta, GA (US)

(73) Assignee: MEDICREA INTERNATIONAL, Neyron (FR)

(*) Notice: Subject to any disclaimer, the term of this patent is extended or adjusted under 35 U.S.C. 154(b) by 41 days.

(21) Appl. No.: 14/511,130

(22) Filed: Oct. 9, 2014

(65) Prior Publication Data

US 2015/0150602 A1    Jun. 4, 2015

(30) Foreign Application Priority Data

Oct. 20, 2013  (FR) ...................... 13 59987

(51) Int. Cl.
*A61B 17/70*    (2006.01)

(52) U.S. Cl.
CPC ....... *A61B 17/7002* (2013.01); *A61B 17/7007* (2013.01); *A61B 17/7047* (2013.01); *A61B 17/7049* (2013.01); *A61B 17/7056* (2013.01); *A61B 17/7071* (2013.01)

(58) Field of Classification Search
CPC ............ A61B 17/7008; A61B 17/7056; A61B 17/7071; A61B 17/7001; A61B 17/7032; A61B 17/7047; A61B 2017/681; A61B 17/70; A61B 17/7007; A61B 17/7062; A61B 17/7064; A61B 17/7067; A61B 17/707
See application file for complete search history.

(56) References Cited

U.S. PATENT DOCUMENTS

| | | | |
|---|---|---|---|
| 5,000,165 A * | 3/1991 | Watanabe | 606/250 |
| 5,005,562 A * | 4/1991 | Cotrel | 606/330 |
| 5,306,275 A * | 4/1994 | Bryan | 606/914 |
| 5,688,274 A * | 11/1997 | Errico et al. | 606/276 |
| 6,716,218 B2 * | 4/2004 | Holmes et al. | 606/105 |
| 7,959,655 B2 * | 6/2011 | Kawakami et al. | 606/276 |
| 8,992,575 B1 * | 3/2015 | Di Lauro et al. | 606/253 |
| 2002/0120272 A1 * | 8/2002 | Yuan et al. | 606/61 |
| 2006/0084990 A1 * | 4/2006 | Gournay | A61B 17/7007 606/276 |
| 2007/0233256 A1 * | 10/2007 | Ohrt | A61F 2/4405 623/17.11 |
| 2011/0087288 A1 * | 4/2011 | Stevenson et al. | 606/250 |
| 2015/0374416 A1 * | 12/2015 | Warren | A61B 17/7001 606/247 |

FOREIGN PATENT DOCUMENTS

| | | |
|---|---|---|
| FR | 2735351 | 12/1996 |
| FR | 2930719 | 11/2009 |
| WO | WO 2011053962 | 5/2011 |

* cited by examiner

*Primary Examiner* — Lynnsy Summitt
(74) *Attorney, Agent, or Firm* — Law Offices of Steven W. Weinrieb

(57) ABSTRACT

An assembly is disclosed for treating an isthmic fracture. It also relates to an assembly which includes materials and instruments for utilizing the assembly in connection with treating the fracture.

9 Claims, 4 Drawing Sheets

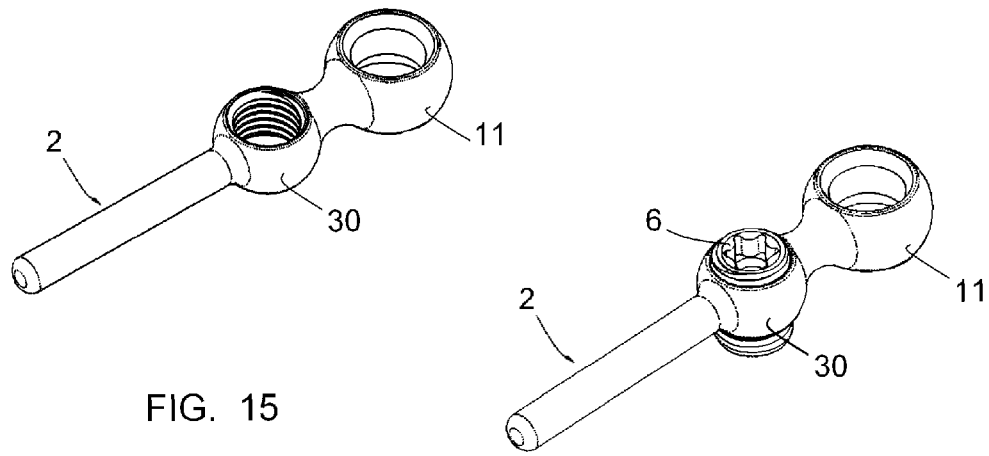
FIG. 15
FIG. 16
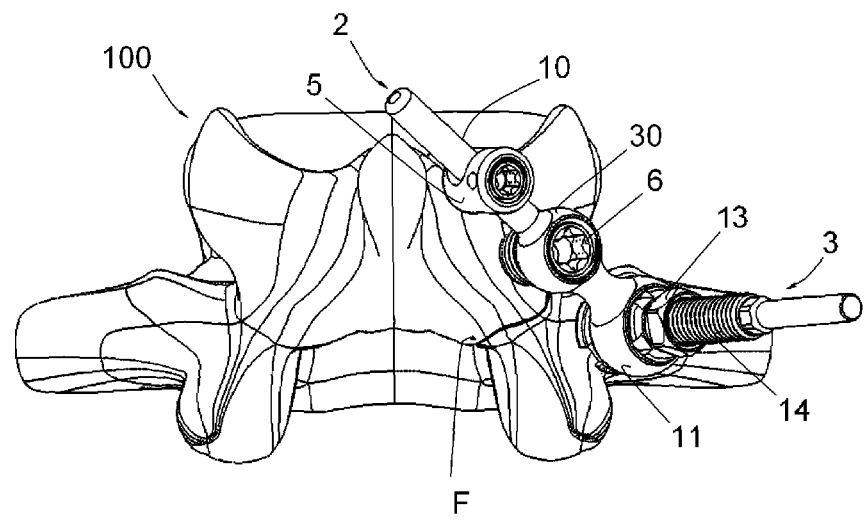
FIG. 17

ASSEMBLY FOR TREATING AN ISTHMIC FRACTURE

FIELD OF THE INVENTION

The present invention relates to an assembly for treating an isthmic fracture. It also relates to an assembly including materials and instruments for utilizing the assembly in connection with the fracture.

BACKGROUND OF THE INVENTION

As is known, on a vertebra, the isthmus is the bone part that joins the vertebral lamina, the pedicle and the base of the transverse process.

This bone part is susceptible to fracture, called "isthmic lysis", which is a stress fracture favored by particular anatomical conditions and/or repeated professional or athletic stresses, and hyperlordosis. This pathology particularly affects workers performing heavy work and major athletes.

One known technique for treating isthmic fracture is called "bi-sectional", i.e., it consists of implanting immobilizing material not only on the affected vertebra but also on one of the two adjacent vertebrae. This technique has the significant drawback of immobilizing a healthy vertebral joint.

Another known technique for treating such a pathology is called "mono-sectional", i.e., it consists of implanting immobilizing material only on the affected vertebra. To date, no material exists that is specifically designed to treat an isthmic fracture, and a practitioner is must perform a more or less empirical mounting, using existing components of other types of materials that are not specifically intended for that indication. Such assemblies do not allow perfect rehabilitation of the fracture or perfect maintenance of the fractured parts for the time that the bone consolidation is done. These parts in particular tend to slide against one another when the fracture is reduced.

OBJECTS OF THE INVENTION

The invention aims to resolve the aforementioned problems by providing materials or assemblies specifically adapted to the treatment of an isthmic fracture, using a mono-sectional technique, which allows perfect rehabilitation of the fracture and perfect maintenance of the fractured parts for the time necessary for the bone consolidation to occur.

SUMMARY OF THE INVENTION

To achieve the aforementioned aim, the material according to the invention comprises:
  a rigid rod having a rod portion and an eyelet at a first end of that rod portion;
  a pedicle screw having a receiving zone on which said eyelet is capable to be engaged;
  at least one hook comprising a curved part capable to be engaged on the lamina of the vertebra, and a body pierced with a conduit designed to receive said rod portion in a location near a second end of that portion, opposite said first end; said hook comprises immobilizing means, for immobilizing it in position along said rod portion;
  a set screw, and
  mounting means arranged on said rod portion, allowing that set screw to be mounted on said rod portion and allowing said screw to be screwed toward the outer bone portion of the isthmus of the treated vertebra, such that that screw exerts pressure against that outer bone part.

In practice, the pedicle screw is placed in the pedicle of the affected vertebra, then the assembly comprising the rigid rod, the set screw, engaged without tightening in said mounting means, and said hook, engaged without immobilization on the rod portion, is placed on the vertebra, by engaging the eyelet on the receiving zone comprised by the pedicle screw; the hook is next engaged behind the lamina of the treated vertebra, then a force is exerted on the material so as to bring the pedicle screw and the hook closer together in order to reduce the fracture; when that reduction is done, the hook is immobilized relative to the rod portion, by action on said immobilizing means; the set screw is next screwed into said mounting means so as to exert pressure on the outer bone part of the isthmus, in order to prevent any risk of insufficient pressure of that outer bone part against the inner bone part and therefore any risk of sliding of that outer bone part against that inner bone part.

Preferably, the material comprises two hooks as previously cited, whereof a first hook comprises a conduit having an axis extending in a first direction relative to a first median plane of said curved part comprised by said first hook, and whereof the second hook comprises a conduit having an axis extending in a second direction relative to a second median plane of the curved part comprised by that second hook, the angle of said first direction with respect to said first median plane being the same than the angle of said second direction with respect to said second median plane; the material thus includes a hook suitable for treating an isthmic fracture extending on the left side of the vertebra and a hook suitable for treating an isthmic fracture extending on the right side of the vertebra.

In this way, a same pedicle screw, a same rigid rod, a same set screw and a same mounting means can be combined with the hook suitable for treating the fracture in question, whether that fracture is located on the left side or on the right side of the vertebra. As a result, the material according to the invention, comprising the two aforementioned hooks, is completely versatile.

Preferably, the conduit comprised by each hook is configured and sized so as to allow, when the hook is engaged on said rod portion, an orientation of the median plane of said curved part of the hook by an angle of 25° to 70° relative to the axis of that rod portion.

This possibility of orienting the hook relative to the rod portion allows perfect pairing of the hook behind the vertebral lamina, regardless of the orientation of said rod portion relative to that lamina.

According to one preferred embodiment of the invention, in that case, said conduit emerges outside the body of the hook through oblong openings and has a flared shape between each of said openings and a central point of the length of that conduit, that conduit being dimensioned to allow travel of the hook relative to said rod portion in a plurality of angular positions in which said median plane forms, with the axis of said rod portion, said angle comprised between 25° and 70°.

Preferably, the axis of the eyelet forms, on the proximal side of that eyelet, an angle of approximately 80° with the longitudinal axis of said rod portion.

This arrangement makes it possible to best orient this rod portion when the eyelet is in place on said receiving zone comprised by the pedicle screw.

It will be understood that the term "proximal" refers to the side of the eyelet that is furthest from the vertebra after placement.

According to one embodiment of the invention, said mounting means is formed by a mounting piece for mounting the set screw on said rod portion, having a conduit such that said mounting piece is capable to be engaged in an adjusted manner on said rod portion, a tapped orifice for receiving the set screw, and tightening means making it possible to immobilize that mounting piece in a given position along said rod portion.

As long as said tightening means are not tightened, the mounting piece is slidable along said rod portion; if the cross-section of the rod portion is circular, said piece is also pivotable relative to said rod portion; this or these mobilities make it possible to choose the most appropriate position of that mounting piece based on the pressure to be exerted on said outer bone zone; when that appropriate position is determined, the tightening means are tightened so as to immobilize the mounting piece relative to the rod portion.

The mounting piece can in particular be made up of a piece with a U-shaped profile, whereof the intermediate part and the base of the parallel branches form said conduit for the adjusted engagement of that piece on said rod portion, and whereof the two parallel branches comprise two coaxial holes for receiving the set screw; one of those holes, situated on the proximal branch, is smooth, and the other hole, situated on the distal branch, is tapped and forms the aforementioned tapped orifice; said set screw comprises a head capable of bearing against said proximal branch when the set screw is screwed into said tapped orifice, so as to bring the proximal and distal branches closer to each other and, in so doing, contain said conduit of the mounting piece on the rigid rod until that mounting piece is immobilized on that rod.

Thus, the aforementioned tightening means are made up of the set screw itself.

Alternatively, the mounting piece can include tightening means independent from the set screw; in particular, the mounting piece can be a single piece and comprise, aside from said conduit for engagement on said rigid rod and said tapped orifice, a tapped hole in emerging in that conduit, in which a screw can be screwed so as to immobilize the mounting piece relative to the rigid rod.

According to another embodiment of the invention, said mounting means is formed by a second tapped eyelet, formed on said rod portion, in which said set screw is capable to be screwed.

The material according to this embodiment has the advantage of being easier to place than the material according to the other embodiment, but allows less precision in the positioning and orientation of the set screw relative to the fractured vertebral zone.

The invention also relates to an assembly including the material as described above and instruments for placing that material; according to the invention, this assembly comprises an instrument forming a clamp, able to bear on the one hand against said pedicle screw and/or against said eyelet, and on the other hand, against said hook, and exerting a force on said pedicle screw and said hook tending to bring the pedicle screw closer to the hook in order to reduce the isthmic fracture.

The invention will be well understood, and other features and advantages thereof will appear, using the following description, done in reference to the appended diagrammatic drawing, which shows, as non-limiting examples, two possible embodiments of the material in question.

BRIEF DESCRIPTION OF THE DRAWINGS

FIG. 15 is a view of the rigid rod according to a second embodiment;

FIG. 16 is a view of that rigid rod after placement of the set screw thereon; and FIG. 17 is a view of a vertebra similar to FIG. 14 during the placement of the material including the rigid rod according to the second embodiment.

DESCRIPTION OF THE PREFERRED EMBODIMENTS

Figure 1:
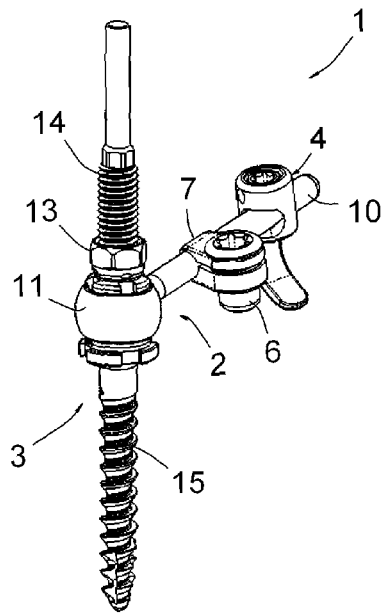
FIG. 1 is a perspective view of a mounting done from elements according to a first embodiment and part of that material, that mounting being designed to treat a fracture situated on the left side of a vertebra.
Figure 2:
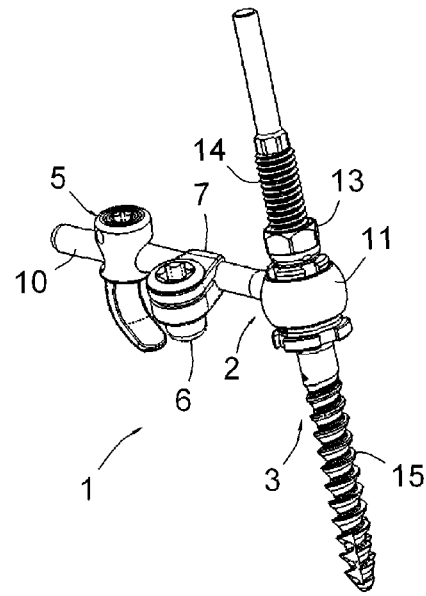
FIG. 2 is a perspective view of another mounting done from elements according to this first embodiment and part of this material, said mounting being designed to treat a fracture situated on the right side of a vertebra.

FIGS. 1 and 2 each show a mounting 1 for treating an isthmic fracture, i.e., a fracture F as shown in FIGS. 12 to 14 and 17, occurring at the bone part that joins the vertebral lamina, the pedicle and the base of the transverse process.

Each mounting 1 is made from elements 2 to 7 that are part of the same material, i.e.: a rigid rod 2, a pedicle screw 3, a left laminar hook 4, a right laminar hook 5, a set screw 6 and a mounting piece 7.

Figure 3:
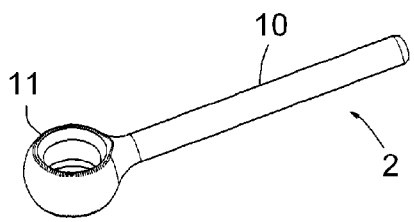
FIG. 3 is a perspective view of a rigid rod with eyelet comprised by said material.
Figure 4:
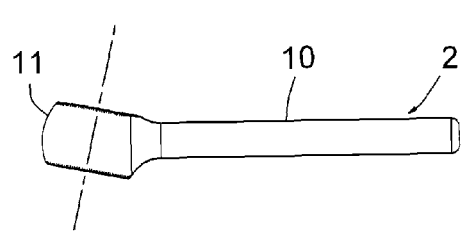
FIG. 4 is a side view of said rod.

In reference to FIGS. 3 and 4, it appears that the rigid rod 2 has a rectilinear rod portion 10 with a circular section, and an eyelet 11 arranged at a first end of that portion 10, forming a body with the portion 10. That eyelet 11 is designed to be engaged on a receiving wall 12 (see FIG. 12) formed by the pedicle screw 3 and to receive a nut 13 (see FIG. 13), engaged on a threaded proximal slug 14 comprised by that screw 3, said nut 13 ensuring blocking of the eyelet 11 on the receiving wall 12.

The axis of the eyelet 11 forms, on the proximal side of that eyelet, an angle of approximately 80° with the longitudinal axis of the portion 10.

The pedicle screw 3 is a so-called "polyaxial" screw, with a structure well known in itself, comprising a base 15 designed to be screwed in the pedicle of a vertebra 100, the aforementioned threaded proximal slug 14 and a ball joint joining said slug 14 to said base 15. That joint is in particular made using a sphere integral with the base of the slug 14, engaged in a cavity formed in the upper end of the base 15 and retained in that cavity by said wall 12. The latter is secured to the base 15, surrounds said cavity and is crimped on said sphere. A screw of this type is described in patent application no. WO 98/55038, to which reference may be made for further details on this screw structure.

Figures 5, 6:
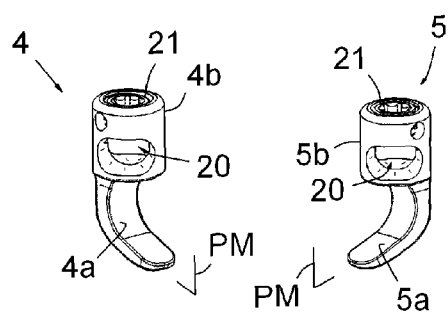
FIGS. 5 and 6 are perspective views of two laminar hooks comprised by said material.
Figure 9:
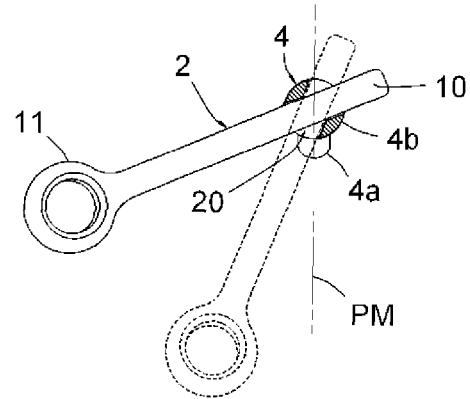
FIG. 9 is a top view of the hook shown in FIG. 5, in cross-section passing through a conduit comprised by that hook, and of the rigid rod engaged in that conduit, the rod being shown, in solid lines, in a first orientation position relative to the hook, and in broken lines, in a second orientation position relative to that hook.

In reference also to FIGS. 5 and 6, it appears that each hook 4, 5 comprises a curved part 4*a*, 5*a* able to be engaged on the lamina of the treated vertebra 100, and a body 4*b*, 5*b* pierced with a conduit 20 designed to receive said portion 10 of the rod 2, in a location close to the second end of that portion 10, opposite said first end. Each conduit 20 passes through the body 4*b*, 5*b* and emerges on the outside of that body through oblong openings; as shown in FIG. 9 regarding the hook 4 (the same is true for the hook 5), that conduit 20 has a flared shape between each of those openings and a central point of its length, such that it allows travel of the hook 4 relative to the portion 10 of the rod 2 in a plurality of angular positions; that travel is possible between the position of the rod 2 shown in solid lines, in which the axis of the portion 10 forms an angle of approximately 70° with the median plane PM of the curved part 4*a*, and the position of the rod 2 shown in broken lines, in which the axis of the portion 10 forms an angle of approximately 25° with that same median plane PM.

The body 4*b*, 5*b* of each hook 4, 5 is further pierced with a tapped bore extending between the conduit 20 and one face of that body opposite the curved part 4*a*, 5*a*. That tapped bore receives a threaded stopper 21 able to bear against the portion 10 of the rod 2 when it is tightened and thereby immobilize the hook 4, 5 relative to that portion 10.

Furthermore, examining FIGS. 5 and 6 simultaneously, it appears that the hook 4 comprises a conduit 20 having an axis extending in a first direction relative to said median plane PM (on the left of that drawing as shown in FIG. 5), while the hook 5 comprises a conduit 20 having an axis extending in a second direction relative to that median plane PM (on the right side of that drawing as shown in FIG. 5); said first direction and said second direction are symmetrical to one another relative to the median planes PM of the two hooks 4, 5 when those median planes are combined.

Figures 7, 8:
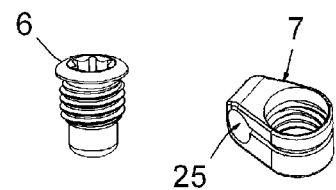
FIG. 7 is a perspective view of a set screw comprised by said material.
FIG. 8 is a perspective view of a mounting piece making it possible to mount said set screw on said rigid rod.

In reference to FIG. 7, it appears that the set screw 6 has a proximal collar, designed to bear against the mounting piece 7 (see FIGS. 1, 2, 10, 11), and a rounded distal end designed to exert pressure against the outer bone part of the vertebral isthmus.

Figure 10:
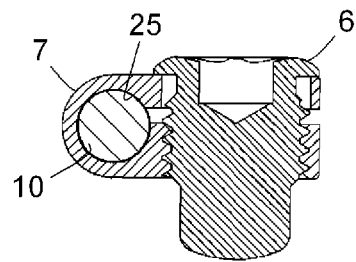
FIG. 10 is an axial cross-sectional view of the set screw and the mounting piece, in a first engaged state of that set screw relative to that part.
Figure 11:
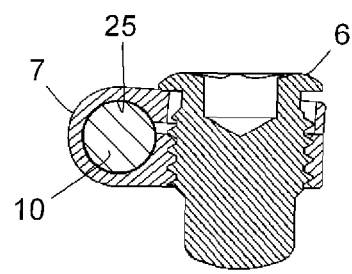
FIG. 11 is a view similar to FIG. 10, in a second engaged state of the set screw relative to the mounting piece.

In reference to FIGS. 8, 10 and 11, it appears that the mounting piece 7 has a U-shaped profile, i.e., comprises an intermediate part and parallel branches. That intermediate part and the base of those parallel branches form a conduit 25 allowing the adjusted engagement of the part 7 on said rod portion 10. The two parallel branches comprise two coaxial holes for receiving the set screw 6; one of those holes, situated on the proximal branch, is smooth, and the other hole, situated on the distal branch, is tapped and able to receive the set screw 6 therein by screwing. As understood in reference simultaneously to FIGS. 10 and 11, before tightening of the screw 6 in those holes (see FIG. 10), the intermediate part and the base of those parallel branches of the part 7 do not grip the portion 10 in the conduit 25, such that that part 7 is slidable and pivotable along the rod portion 10; after tightening the screw 6 in those holes (see FIG. 11), the parallel branches of the part 7 are brought closer to each other, which results in pressing said intermediate part and the base of the parallel branches on the rod portion 10, and, in so doing, immobilizing the mounting piece 7 on that rod portion 10.

Figure 12:
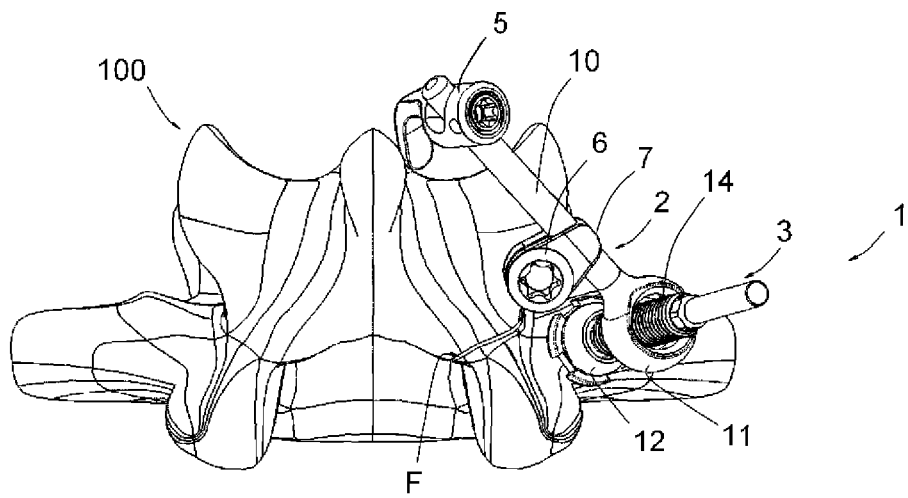
FIG. 12 is a rear view of a vertebra on which the material according to FIG. 2 is being placed.

In practice, as shown in FIG. 12, the pedicle screw 3 is placed in the pedicle of the vertebra 100 in question, then the assembly comprising the rigid rod 2, the set screw 6, engaged without tightening in the mounting piece 7, and the appropriate hook 4 or 5 (this is the hook 5 in the case at hand, the fracture F being on the right side of the vertebra 100), engaged on the rod portion 10 without tightening the stopper 21, is placed on the vertebra 100, by engaging the eyelet 11 on the receiving wall 12 comprised by the pedicle screw 3.

Figure 13:
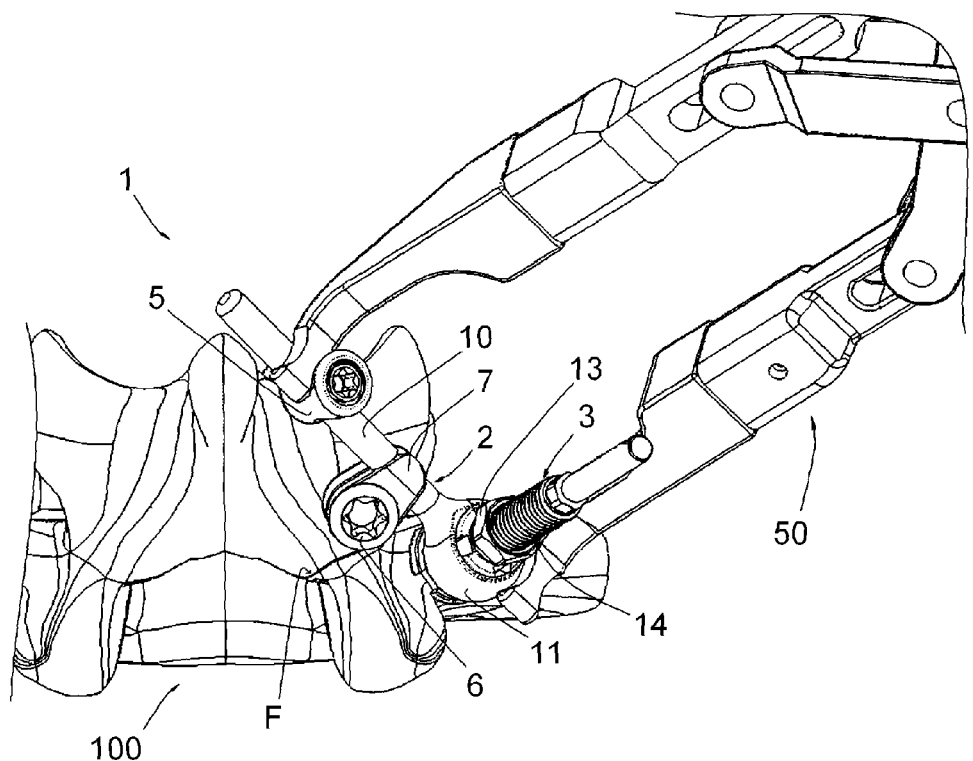
FIGS. 13 and 14 are views similar to FIG. 12, during two subsequent steps of the process for placing that material.

The nut 13 is placed on the threaded slug 14 of the screw 3 and the hook 5 is engaged behind the lamina of the vertebra 100, than a force is exerted on the mounting 1 using an instrument 50 forming a clamp, so as to bring the pedicle screw 3 and the hook 5 closer together in order to reduce the isthmic fracture F (see FIG. 13).

When this reduction is done, the hook 5 is immobilized relative to the rod portion 10, by tightening the stopper 21. The slug 14 is sectioned above the nut 13.

Figure 14:
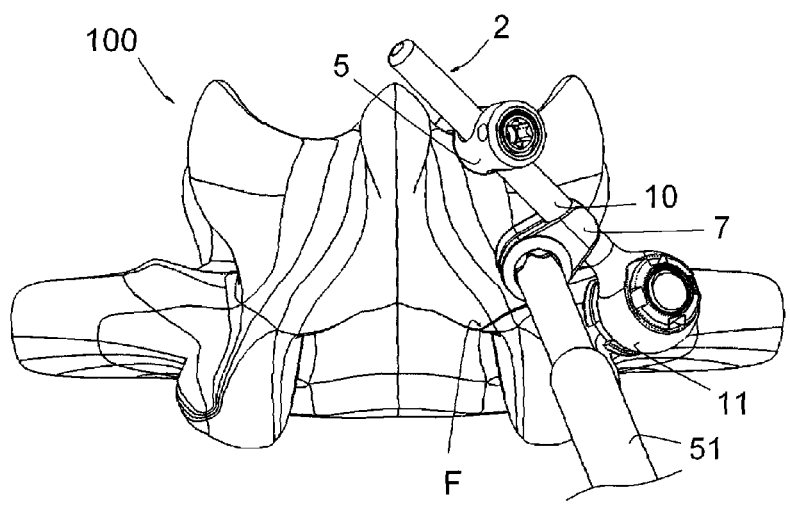

The mounting piece 7, which is then slidable along the rod portion 10 and pivotable relative thereto, is brought into the most appropriate position depending on the pressure to be exerted on said outer bone zone of the fractured isthmus; when that appropriate position is determined, the set screw 6 is screwed into the tapped orifice of the mounting piece 7, using a screwdriver 51, so as simultaneously to immobilize the mounting piece 7 relative to the rod portion 10 and cause the set screw 6 to exert pressure on the outer bone part of the isthmus (see FIG. 14). This pressure makes it possible to avoid any risk of insufficient pressure of that outer bone part against the inner bone part and therefore any risk of sliding of that outer bone part against that inner bone part.

FIGS. 15 and 16 show another embodiment of the rod 2 (for simplification reasons, the parts or elements already described, that are found in this embodiment, are identified using the same numerical references). In this other embodiment, instead of the mounting piece 7, the rod portion 10 comprises a second, tapped eyelet 30 in which said set screw 6 can be screwed. The mounting is done in the same way as before, see FIG. 17.

As appears from the preceding, the invention provides material for treating an isthmic fracture having the decisive advantages of being specifically suitable for the treatment of an isthmic fracture, with perfect rehabilitation of the fracture and perfect maintenance of the fractured parts for the time necessary for the bone consolidation to occur.

The invention has been described above in reference to embodiments provided purely as an example. It is of course not limited to these embodiments, but extends to all other embodiments covered by the appended claims.

What is claimed is:

1. An assembly for treating an isthmic fracture of a vertebra comprising:
    a rigid rod comprising a rod portion, and an eyelet disposed at a first end of said rod portion;
    a pedicle screw having a receiving zone upon which said eyelet of said rigid rod is capable of being engaged, said pedicle screw being capable of engaging a pedicle portion of the vertebra;
    at least one hook comprising a curved part capable of engaging a lamina portion of the vertebra so as to operatively cooperate with said pedicle screw in drawing the pedicle and lamina portions of the vertebra together, and a body pierced with a conduit designed to receive a second end portion of said rod portion of said rigid rod, which is opposite said first end of said rod portion, said at least one hook comprising immobilizing means adapted to engage said second end portion of said rod portion of said rigid rod for immobilizing said at least one hook in position along said second end portion of said rod portion;

a set screw for engaging an outer bone portion of an isthmus portion of the vertebra, said set screw having a first threaded portion and a second non-threaded portion; and a mounting piece disposed upon said rod portion and having an internally threaded bore for receiving and threadedly cooperating with said first threaded portion of said set screw while said set screw extends through said mounting piece such that said second non-threaded portion of said set screw engages the outer bone portion of the isthmus portion of the vertebra, whereby when said set screw is screwed toward the outer bone portion of the isthmus portion of the vertebra, said first threaded portion of said set screw cooperates with said mounting piece so as to immobilize said mounting piece upon said rod portion while said second non-threaded portion of said set screw exerts a predetermined amount of pressure against the outer bone portion of the isthmus portion of the vertebra so as to bring the outer bone portion of the isthmus portion of the vertebra into contact with an inner bone portion of the isthmus portion of the vertebra.

2. The assembly according to claim 1, wherein said at least one hook comprises two hooks, and wherein a first one of said two hooks comprises the conduit having an axis extending in a first direction relative to a first median plane of said curved part comprised by said first hook, and wherein a second hook of said two hooks comprises a body pierced with a conduit having an axis extending in a second direction relative to a second median plane of a curved part comprised by said second hook, an angle of said first direction with respect to said first median plane being the same as an angle of said second direction with respect to said second median plane said two hooks therefore comprising a hook suitable for treating an isthmic fracture extending on the left side of the vertebra and a hook suitable for treating an isthmic fracture extending on the right side of the vertebra.

3. The assembly according to claim 2, wherein the conduit comprised by each hook is configured and sized so as to allow, when the hook is engaged on said rod portion, an orientation of the median plane of said curved part of the hook by an angle of 25° to 70° relative to a longitudinal axis of the rod portion.

4. The assembly according to claim 3, wherein said conduit of each hook emerges outside the body of each respective hook through oblong openings and has a flared shape between each of said openings and a central point of a length of the conduit, the conduit being dimensioned to allow travel of the respective hook relative to said rod portion in a plurality of angular positions in which said median plane forms, with the axis of said rod portion, said angle comprised between 25° and 70°.

5. The assembly according to claim 1, wherein the eyelet is defined around an axis which forms, on a proximal side of said eyelet, an angle of approximately 80° with a longitudinal axis of said rod portion.

6. The assembly according to claim 1, wherein said mounting piece is adapted for mounting the set screw on said rod portion, has a conduit such that said mounting piece is capable of being engaged in an angularly adjustable manner on said rod portion, and can be fixedly secured at a predetermined position along said rod portion.

7. The assembly according to claim 6, wherein the mounting piece is made of a piece with a U-shaped profile comprising two parallel branches, wherein an intermediate part of said mounting piece and said two parallel branches of said mounting piece form said conduit through which said rod portion can pass and along which, and around which, said mounting piece can be longitudinally and angularly adjusted with respect to said rod portion, and wherein further, a first one of said two branches comprises a smooth hole, and a second one of said two branches comprises said internally threaded bore, said smooth hole and said internally threaded bore being coaxial and configured to receive the set screw; said set screw comprises a head capable of bearing against the first one of said two branches when the set screw is screwed into said internally threaded bore so as to bring the two parallel branches closer to each other and, in so doing, effectively immobilize said mounting piece on the rigid rod.

8. The assembly according to claim 1, wherein the assembly comprises a clamp-type instrument able to bear on the one hand against said pedicle screw and/or against said eyelet, and on the other hand, against said at least one hook, and capable of exerting a force on said pedicle screw and said hook tending to bring the pedicle screw closer to the hook in order to reduce the isthmic fracture.

9. An assembly for treating an isthmic fracture of a vertebra comprising:

a rigid rod comprising a rod portion, and a first eyelet disposed at a first end of said rod portion;

a pedicle screw having a receiving zone upon which said first eyelet of said rigid rod is capable of being engaged, said pedicle screw being capable of engaging a pedicle portion of a vertebra;

at least one hook comprising a curved part capable of engaging a lamina portion of the vertebra so as to operatively cooperate with said pedicle screw in drawing the pedicle and lamina portions of the vertebra together, and a body pierced with a conduit designed to receive a second end portion of said rod portion of said rigid rod, which is opposite said first end of said rod portion, said at least one hook comprising immobilizing means adapted to engage said second end portion of said rod portion of said rigid rod for immobilizing said at least one hook in position along said second end portion of said rod portion;

a set screw for engaging an outer bone portion of an isthmus portion of the vertebra, said set screw having a first threaded portion and a second non-threaded portion; and a second eyelet fixedly formed upon said rod portion and having an internally threaded bore for receiving and threadedly cooperating with said first threaded portion of said set screw while said set screw extends through said second eyelet such that said second non-threaded portion of said set screw engages the outer bone portion of the isthmus portion of the vertebra, whereby when said set screw is screwed toward the outer bone portion of the isthmus portion of the vertebra, said threaded engagement of said first threaded portion of said set screw cooperates with said internally threaded bore of said second eyelet so as to positionally adjust a disposition of said set screw with respect to said second eyelet while said second non-threaded portion of said set screw projects outwardly from said second eyelet and extends toward the outer bone portion of the isthmus portion of the vertebra so as to exert a predetermined amount of pressure against the outer bone portion of the isthmus portion of the vertebra so as to bring the outer bone portion of the isthmus portion of the vertebra into contact with an inner bone portion of the isthmus portion of the vertebra.

\* \* \* \* \*